United States Patent
Lasko

(10) Patent No.: US 6,692,811 B1
(45) Date of Patent: *Feb. 17, 2004

(54) SUBSTRATES COMPRISING FLOCKED FIBERS OF SUPERABSORBENT POLYMER

(75) Inventor: Vincent P. Lasko, New Egypt, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/356,948

(22) Filed: Jul. 19, 1999

(51) Int. Cl.[7] .................................................. B05D 1/14
(52) U.S. Cl. .................... 428/90; 604/378; 604/384; 604/367
(58) Field of Search ............................. 428/90, 93, 94, 428/95, 96, 97; 442/375; 427/200, 206; 604/378, 367, 368, 370, 369, 371, 372, 373, 374, 375, 376, 377, 384, 365

(56) References Cited

U.S. PATENT DOCUMENTS

| | | | |
|---|---|---|---|
| 2,527,501 A | | 10/1950 | Saks |
| 2,691,611 A | | 10/1954 | Saks |
| 3,436,442 A | | 4/1969 | Saks |
| 3,672,929 A | | 6/1972 | Riordan |
| 3,815,341 A | * | 6/1974 | Hamano ...................... 55/477 |
| 3,967,623 A | | 7/1976 | Butterworth et al. |
| 4,062,779 A | * | 12/1977 | Nakamura et al. ........... 210/386 |
| 4,857,377 A | * | 8/1989 | Daimon et al. ................ 428/90 |
| 5,002,814 A | | 3/1991 | Knack et al. |
| 5,577,494 A | * | 11/1996 | Kuypers et al. ........ 128/201.13 |
| 5,591,149 A | | 1/1997 | Cree et al. |
| 5,603,946 A | * | 2/1997 | Constantine ................. 424/445 |
| 5,624,729 A | | 4/1997 | Cohen et al. |
| 5,821,179 A | * | 10/1998 | Masaki et al. ............... 442/375 |
| 6,365,794 B1 | * | 4/2002 | Dabi et al. ................... 604/367 |

FOREIGN PATENT DOCUMENTS

| | | |
|---|---|---|
| EP | 0 737 462 A1 | 10/1996 |
| EP | 0861646 | 9/1998 |
| WO | 95/13773 | 11/1994 |
| WO | WO 98/25560 | 6/1998 |
| WO | WO 98/36722 | 8/1998 |

OTHER PUBLICATIONS

U.S. patent application Ser. No. 09/532,239 w/ copy of allowed claims.
Copy of European Search Report (Appln. No. EP 00 11 5483).

* cited by examiner

Primary Examiner—Weilun Lo
Assistant Examiner—Michele Kidwell

(57) ABSTRACT

A substrate having flocked fibers of superabsorbent polymer thereon is provided. The substrate may be one of a variety of materials, such as nonwoven materials, polymer films, apertured films, absorbent layers, netting, woven fabrics, foams, reticulated films and the like.

5 Claims, 3 Drawing Sheets

SUBSTRATES COMPRISING FLOCKED FIBERS OF SUPERABSORBENT POLYMER

The present invention relates to substrates, particularly for use in absorbent articles, comprising flocked fibers of superabsorbent polymer.

BACKGROUND OF THE INVENTION

The use of superabsorbent polymers in absorbent articles, such as sanitary napkins, pantiliners, diapers, and incontinence pads is known. Superabsorbent polymers enhance the liquid management properties of absorbent articles, such as capacity and retention of fluids. They are added to the components of absorbent articles in the form of particles or fibers, but most often in the form of particles. Most commercially available processing equipment is designed to handle superabsorbent polymer particles rather than fibers, since fibers are more difficult to disperse than particles and tend to collapse.

Superabsorbent polymers are typically found in the absorbent core of an absorbent article, where they are easily incorporated. However, it would be desirable to be able to employ superabsorbent polymers in a convenient manner in and on other kinds of substrates, such as other nonwoven materials, polymer films, apertured films, netting, woven fabrics, foams, reticulated films, and the like.

Flocking is a technique by which fibers are fixed in a vertical position on a substrate, and is primarily used in the fabric industry. However, EP 0 737 462 A1 discloses a laminated material to cover the outside of an absorbent product, characterized in that at least one portion of the surface of the laminated material bears a layer of fibers applied by flocking. The flocked fibers are thereby located on the external surface of the absorbent product in order to give the absorbent product improved tactile properties over products that employ plastic films against the skin. EP 0 737 462 A1 discloses that the external surface to which the flocked fibers may be applied may be a perforated cover. The cover may be perforated before or after the flocking is applied, but is preferably perforated before flocking.

Applicant has discovered that fibers of superabsorbent polymer may be advantageously adhered to a variety of substrates by flocking. According to the invention, when flocked fibers of superabsorbent polymer are applied to a substrate, they stand in an upright, vertical manner on the surface. Such an orientation allows the flocked fibers of superabsorbent polymer to absorb an increased amount of fluid compared with unflocked fibers of superabsorbent polymer, i.e., fibers compressed horizontally. This in turn makes substrates comprising flocked fibers of superabsorbent polymer particularly attractive for use in absorbent articles of all types.

Applicant has also discovered that flocked fibers of superabsorbent polymer may advantageously be applied to the surface of an apertured film. In particular, an apertured film comprising flocked fibers of superabsorbent polymer on its underside surface, and additionally on the outer surfaces of the aperture sidewalls, provides an improved cover or other component of an absorbent article. Materials and manufacturing technology have enabled the development of nonwoven fabric and polymer apertured films that mimic the feel of woven fabric quite well. And although many variations of apertured films exist in the art, improved apertured films are always desired, particularly those having improved fluid transport properties.

SUMMARY OF THE INVENTION

The present invention provides substrate having flocked fibers of superabsorbent polymer thereon, as well as an absorbent article comprising such as substrate.

The invention also provides an apertured film having flocked fibers of superabsorbent polymer thereon. The flocked fibers of superabsorbent polymer may be on the top surface or the underside surface of the apertured film, or on the sidewalls of the apertures themselves.

BRIEF DESCRIPTION OF THE INVENTION

DETAILED DESCRIPTION OF THE INVENTION

Figure 1:
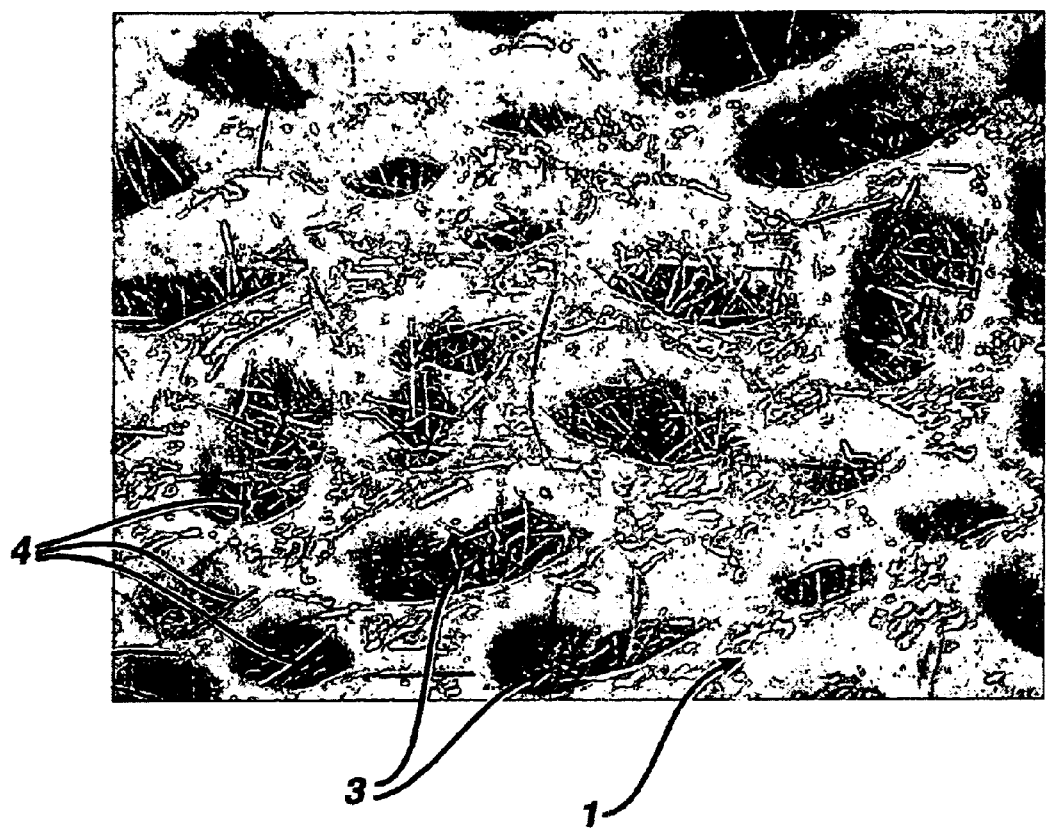
FIG. 1 is a magnified view of the top surface of an apertured film with flocked fibers of superabsorbent polymer, rayon, and polyester adhered to the underside thereof.

According to the invention, fibers of superabsorbent polymer are adhered to a substrate by flocking. The substrate may be one of a variety of materials, such as nonwoven materials, polymer films, breathable materials, apertured films, absorbent layers, netting, woven fabrics, foams, and reticulated films. Preferably, the substrate is selected from the group consisting of nonwoven materials, polymer films, breathable materials, apertured films, and absorbent layers. Other substrates suitable for flocking of superabsorbent polymer thereon will be recognized by those skilled in the art, and the invention is not intended to be limited to any particular kind of substrate.

A variety of nonwoven materials are known and used in the field of absorbent articles. They are typically made by entangling, for example via carding or hydroentangling, thermoplastic fibers, such as polyolefin fibers i.e., polyethylene and polypropylene, polyester fibers, polyamide fibers (including nylon), polyacrylic fibers, and the like into a web.

Examples of polymer films include polyethylene, polypropylene, polyester, cellulose, cellophane, polyurethane, cross-linked polyethylene, polyethylene oxide, and polyvinyl alcohol.

Examples of breathable materials include polyurethane films and microporous films in which microporosity is created by ionizing radiation or by leaching out of soluble inclusions using aqueous or nonaqueous solvents. Single or multiple layers of permeable films, fabrics, and combinations thereof that provide a tortuous path, and/or whose surface characteristics provide a liquid surface repellent to the penetration of liquids may also be used.

An apertured films is any type of film having apertures in it. Such films may be made from nonwoven materials, polymer films, breathable materials, and so forth.

Absorbent layers include, for example, those made of loosely associated absorbent hydrophilic material such as cellulose fibers, including wood pulp, regenerated cellulose fibers or cotton fibers, or other absorbent materials generally known in the art, including acrylic fibers, polyvinyl alcohol fibers, peat moss.

The substrate is preferably used as part of an absorbent article, for example a sanitary napkin, pantiliner, diaper, incontinence pad, interlabial article, wound dressing, baby wipe, feminine hygiene wipe, nursing pad, or other similar product for absorbing bodily fluids. Preferably, the absorbent article is a sanitary napkin or a pantiliner. Such sanitary napkin or pantiliner may have an approximately rectangular, oval, dogbone, or peanut shape. Depending on the nature of the absorbent article, its size may vary. For example, sanitary napkins typically have a caliper of about 1.4 to about 5 mm, a length of about 3 to about 16 inches, and a width of about 1 to about 5 inches. Pantiliners typically have a caliper of less than about 0.2 inches, a length of less than about 8 inches, and a width of less than about 3 inches.

Fibers of superabsorbent material are applied to one or more surfaces of the substrate by the process of flocking. Methods of flocking fibers onto a surface are known in the art of fabric manufacture. See for example, U.S. Pat. Nos. 2,527,501; 2,691,611; 3,436,442; and 3,672,929. Typically, a substrate, such as a cover, is coated with adhesive on all or a portion of its surface. The coated substrate is then passed through a fiber metering station in which an electrostatic field is maintained around the substrate, using for example electrodes situated above and below the substrate. The fibers are applied to the adhesive on the substrate in the presence of the electrostatic field, which orients the fibers perpendicular to the substrate as they contact the adhesive. The substrate is then heated, polymerizing the adhesive and anchoring the fibers. Unattached fibers may be vacuumed away.

Preferably, the adhesive employed to attach the fibers to the internal surface is a polymerizable resin, such as modified acrylic water based compounds, for example FLEX-BOND 974, 977, 983, and 986 commercially available from Air Products, CARBOTAC Adhesives (PSAs) commercially available from BF Goodrich, and CARBOBOND Adhesives (non-PSAs) also commercially available from BF Goodrich.

A variety of superabsorbent polymers are known, and any of these may be used according to the invention. Superabsorbent polymer fibers are hydrophilic fibers that are swellable and capable of absorbing greater than about 5 grams per gram (of fiber weight) of 1% saline solution. Examples of superabsorbent polymer fibers are polyacrylate fibers, fibers of grafted cellulose, and fibers of maleic acid. Preferred types of superabsorbent polymer fibers include OASIS Type 101, commercially available from Technical Absorbents Limited and CAMELOT, commercially available from Camelot, Alberta, Canada. The substrate may additionally contain superabsorbent polymer in a form other than as flocked fibers, such as in the form of particles, or non-flocked fibers.

Flocked fibers of a second hydrophilic material, a hydrophobic material, or combinations thereof may also be adhered to the substrate with fibers of the superabsorbent polymer. As used herein, "a second hydrophilic material" means an absorbent material or wettable material other than a superabsorbent polymer. Wettable materials are typically hydrophobic materials that have been treated with a wetting agent to render them hydrophilic. Examples of wettable materials include bicomponent fibers, polypropylene fibers, and polyester fibers that have been treated for example with surfactants. Preferred wettable materials are polyester fibers, such as DuPont-Akra Polyester Type 11A Bright commercially available from DuPont Company treated with a surfactant such as Tween 20 commercially available from ICI Americas Inc. Absorbent materials are hydrophilic materials that both that have an affinity for and absorb fluids, such as rayon, acrylics, nylon, polyvinyl alcohol, and natural or regenerated cellulosics. A preferred type of absorbent material is rayon.

Hydrophobic materials include certain olefins and large denier polyester fibers, preferably having a denier of at least 3, more preferably at least 6. A preferred hydrophobic material is 15 denier polyester commercially available from DuPont Company.

In a preferred embodiment of the invention, the flocked fibers comprise a combination of superabsorbent polymer and a second hydrophilic material (i.e., a wettable material, absorbent material, or both). In this embodiment, fluid is quickly absorbed by the fibers of second hydrophilic material and then transferred to the fibers of superabsorbent polymer. Although the fibers of superabsorbent polymer absorb more slowly than the fibers of second hydrophilic material, the superabsorbent polymer fibers have overall higher capacity and increased fluid retention.

In this embodiment, the amount of superabsorbent polymer in the combined superabsorbent polymer/second hydrophilic material fibers is typically from about 5 to about 95 percent by weight, preferably from about 30 to about 70 percent by weight. The flocked fibers of superabsorbent polymer may be uniformly dispersed in the fibers of second hydrophilic material, or the fibers of superabsorbent polymer and second hydrophilic material may be adhered to the substrate in patterns.

In a particularly preferred embodiment of the invention, the flocked fibers comprise a combination of superabsorbent polymer, a second hydrophilic material, and a hydrophobic material. Again, fluid is quickly absorbed by the fibers of the second hydrophilic material and transferred to the higher fluid capacity superabsorbent polymer fibers. The fibers of hydrophobic material absorb little or no fluid and therefore advantageously maintain their physical integrity, such as to minimize wet collapse. The hydrophobic fibers support the fibers of superabsorbent polymer and second hydrophilic material as the latter absorb fluid and lose their rigidity. Moreover, due to the upright support of the hydrophobic fibers, less pressure is placed on the substrate, also increasing the absorbent capacity of the substrate. In this manner, the overall structure and physical integrity of the substrate is preserved.

In this embodiment, the amount of superabsorbent polymer in the combined superabsorbent polymer/second hydrophilic material/hydrophobic material fibers is typically from about 5 to about 95 percent by weight, preferably from about 30 to about 70 percent by weight. The fibers of superabsorbent polymer may be uniformly dispersed in the other fibers, or the various fibers may be adhered to substrate in patterns.

Regardless of type, the length of the flocked fibers should be less than about 1 mm, preferably less than about 0.8 mm. The denier of the flocked fibers should be in the range of about 1.2 d to about 15 d, preferably about 1.8 d to about 6 d. It is also preferred that the fibers suffer little or no wet collapse.

The flocked fibers may be adhered to all or a portion of the substrate. The flocked fibers may be on one or all sides of the substrate. The same or different flocked fibers may be on two or more different areas of the substrate.

In another embodiment of the invention, the substrate is an apertured film. The apertured film comprises a top surface, an underside surface, and a plurality of apertures. The apertures originate in the top surface and extend through the underside surface of the film. Each of the apertures is defined by a sidewall having an inner surface and an outer surface. The geometry and size of the apertures are not critical to the invention, and a variety of apertured films are known in the art, any of which may be used in the present invention. See for example, U.S. Pat. Nos. 5,824,352 and 5,770,144 and the references cited therein.

The flocked fibers of superabsorbent polymer may be located on the top surface of the apertured film, or the underside surface of the apertured film. Preferably, the flocked fibers are adhered to the underside surface of the apertured film. In addition, the flocked fibers are preferably adhered to the outer surfaces of the aperture sidewalls. The latter advantageously creates tendrils of superabsorbent polymer extending from the end of the aperture sidewalls. These tendrils aid in pulling fluid through the apertures and away from the top surface of the film.

The method of aperturing the film is also not critical to the invention. In general, known methods involve supporting a starting film on the surface of a topographical support member having a pattern of holes and/or other features on its surface. Fluid such as water is directed against the starting film to rupture it and conform its shape to that of the support member's surface. Alternatively, the starting film may be apertured and conformed by drawing a vacuum underneath the starting film. See for example, U.S. Pat. Nos. 5,824,352 and 5,770,144.

The flocking step may take place before or after the film aperturing step. Preferably, flocking is done after aperturing. When applying the adhesive onto an apertured film, care must be taken to apply adhesive only to the land areas of the film.

Figure 2:
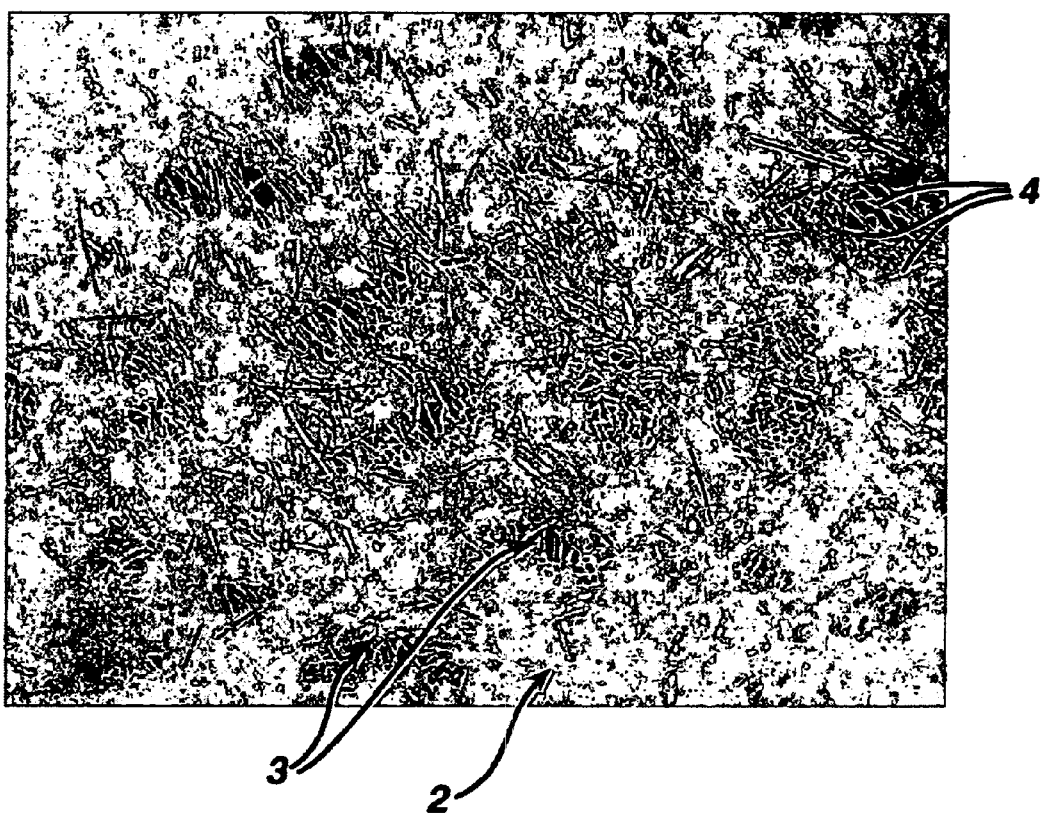
FIG. 2 is a magnified view of the underside surface of the apertured film in FIG. 1.

FIGS. 1 and 2 are magnified views of the top and underside surfaces, respectively, of an apertured film comprising flocked fibers of superabsorbent polymer OASIS Type 101, rayon, and polyester on its underside surface according to the invention. The top surface 1, underside surface 2, and apertures 3 are shown. Flocked fibers 4 are adhered to the underside surface 3 of the film. Note that many of the flocked fibers extend or blossom into the open area of the apertures from the surrounding land area of the film.

Such an apertured film may be used, for example, as either the cover or the backsheet of an absorbent article. Preferably, it is used as the cover of an absorbent article, since a perforated backsheet may leak fluid onto the user's undergarment.

Figure 3:
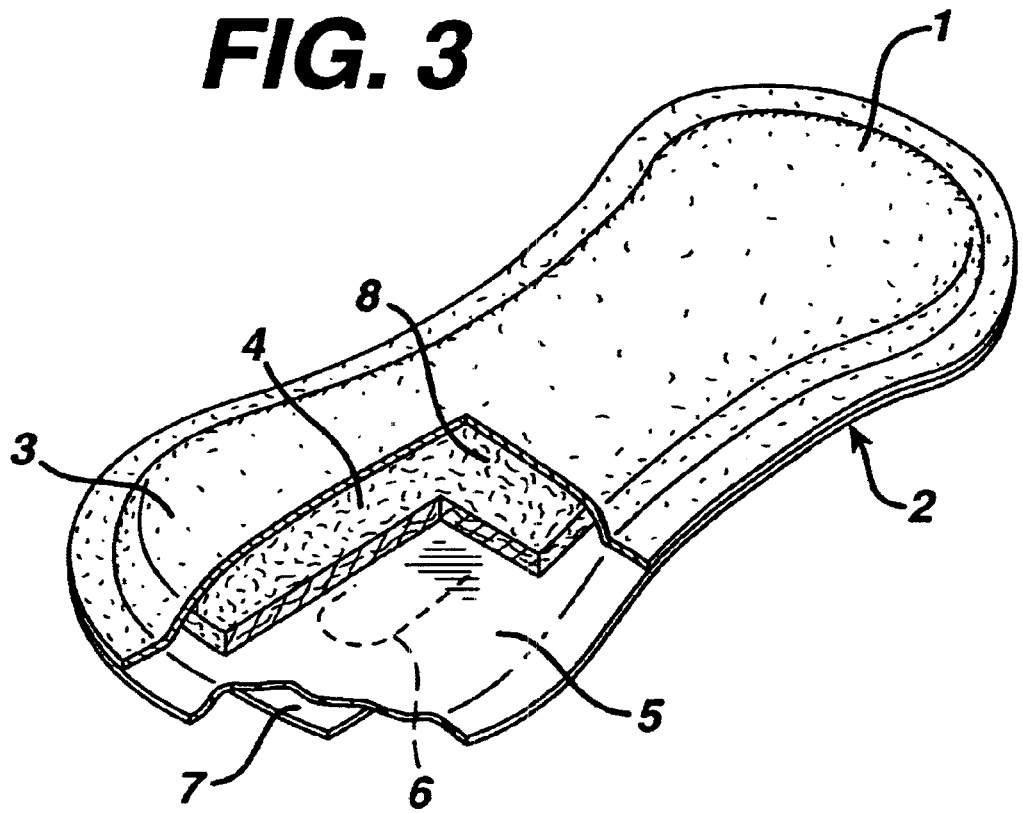
FIG. 3 depicts an absorbent article (pantiliner) having a cover comprising flocked fibers of superabsorbent polymer according to the invention.

FIG. 3 depicts a pantiliner comprising a cover made of an apertured film having flocked fibers of superabsorbent polymer thereon according to the invention. The pantiliner shown in FIG. 3 comprises in sequence from its body-facing surface 1 to its garment-facing surface 2 the cover 3, an absorbent core 8, and a liquid impermeable backsheet 5. The thickness of the cover may vary from approximately 0.001 to 0.062 inch, depending on the material chosen. Generally, cover 3 is a single sheet of material having a width sufficient to form the body-facing surface 1 of the article. The cover may be longer than the absorbent core so as to form transverse ends. The transverse ends may be sealed with other layers to fully enclose the absorbent core.

The absorbent core 8 may be comprised of a loosely associated absorbent hydrophilic material such as cellulose fibers, including wood pulp, regenerated cellulose fibers or cotton fibers, or other absorbent materials generally known in the art, including acrylic fibers, polyvinyl alcohol fibers, peat moss and superabsorbent polymers.

The absorbent article further comprises a liquid impermeable backsheet 5, the exterior of which forms the garment-facing surface of the article. The thickness of the backsheet when formed from a polymeric film typically is about 0.001 to 0.002 inch. A variety of materials are known in the art for use as backsheet, and any of these may be used. Generally, the backsheet 5 is a single sheet of material having a width sufficient to form the garment-facing surface 2 of the absorbent article. The backsheet may extend around the sides of the absorbent core in a C-shaped configuration with the portions of the backsheet adjacent its longitudinal edges extending upwardly from the garment-facing surface toward the body-facing surface of the article. Preferably the backsheet is made of a breathable material.

The absorbent article may be applied to the crotch of underpants by placing the garment-facing surface 2 of the absorbent article against the inside surface of the crotch of the underpants. Strips of pressure sensitive adhesive 6 may be applied to the garment-facing surface 2 of the absorbent article to help maintain it in place. As used herein, the term "pressure-sensitive adhesive" refers to any releasable adhesive or releasable tenacious means. Suitable pressure sensitive adhesives include for example water-based adhesives such as acrylate adhesives. Alternatively, the adhesive may comprise rapid setting thermoplastic "hot melt" rubber adhesives or two-sided adhesive tape.

A paper release strip 7 that has been coated on one side may be applied to protect the strips of adhesive 6 prior to use. The coating, for example silicone, reduces adherence of the coated side of the release strip to the adhesive. The release strip can be formed from any suitable sheet-like material which, when coated, adheres with sufficient tenacity to the adhesive to remain in place prior to use but can be readily removed when the absorbent article is to be used.

The absorbent article may comprise other known materials, layers, and additives, such as transfer layers, foam layers, odor control agents, medicaments, and the like, many examples of which are known in the art. A transfer layer in particular, however, may advantageously be unnecessary in the present absorbent article, as further explained below. The absorbent article can optionally be embossed with decorative designs using conventional techniques.

The following non-limiting examples further illustrate the invention.

EXAMPLE 1

An absorbent core comprising flocked fibers of superabsorbent polymer was prepared as follows.

A one ounce per square yard substrate of 100% polyester was used as the carrier fabric. A polymerizable resin was applied in various patterns to the polyester fabric. A fiber blend consisting of 30 percent superabsorbent fibers, 40 percent rayon fibers, and 30 percent polyester fibers was metered on the polyester fabric. The fibers were oriented in the vertical position via an electrostatic field. The fibers adhered where the resin was applied. The substrate was then passed through an oven to polymerize the resin, anchoring the fibers to the polyester fabric. The excess fibers were vacuumed away.

EXAMPLE 2

An apertured film comprising flocked fibers of superabsorbent polymer is prepared as follows.

A starting film of polyethylene is placed over a topographical support member having a pattern of holes thereon. The support member is rotatably mounted on a drum. Water at a temperature of about 160° F. and a pressure of about 1350 psig is directed against the surface of the starting film opposite to the surface contacting the support member, thereby aperturing the starting film.

The film is dried. Flocked fibers comprising a blend of 30 percent superabsorbent fibers, 40 percent rayon fibers, and 30 percent polyester fibers is metered onto the apertured film. The fibers are oriented in the vertical position via an electrostatic field. The fibers adhere where the resin is applied. The substrate is then passed through an oven to polymerize the resin, anchoring the fibers to the polyethylene film. The excess fibers are vacuumed away.

I claim:

1. A substrate having flocked fibers of superabsorbent polymer and flocked fibers of a second hydrophilic material thereon.

2. The substrate of claim 1, wherein the second hydrophilic material is selected from the group consisting of wettable materials, absorbent materials, and mixtures thereof.

3. The substrate of claim 1 further comprising flocked fibers of a hydrophobic material thereon.

4. The substrate of claim 3, wherein the hydrophobic material is selected from the group consisting of polyesters, olefins, and mixtures thereof.

5. The substrate of claim 1, wherein the fiber comprise a combination of superabsorbent polymer, another hydrophilic material, and a hydrophobic material.

* * * * *